US010292575B2

(12) United States Patent
Surti et al.

(10) Patent No.: US 10,292,575 B2
(45) Date of Patent: May 21, 2019

(54) ENDOSCOPE STABILIZATION SYSTEM

(71) Applicant: Cook Medical Technologies LLC, Bloomington, IN (US)

(72) Inventors: Vihar C. Surti, Winston-Salem, NC (US); John Crowder Sigmon, Jr., Greensboro, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 166 days.

(21) Appl. No.: 15/420,194

(22) Filed: Jan. 31, 2017

(65) Prior Publication Data

US 2017/0135562 A1 May 18, 2017

Related U.S. Application Data

(63) Continuation of application No. 13/676,877, filed on Nov. 14, 2012, now Pat. No. 9,585,546.

(60) Provisional application No. 61/562,137, filed on Nov. 21, 2011.

(51) Int. Cl.
| A61B 1/00 | (2006.01) |
| A61B 1/005 | (2006.01) |
| A61B 1/012 | (2006.01) |
| A61B 1/008 | (2006.01) |
| A61B 1/01 | (2006.01) |
| A61B 1/31 | (2006.01) |

(52) U.S. Cl.
CPC .......... *A61B 1/00154* (2013.01); *A61B 1/008* (2013.01); *A61B 1/0055* (2013.01); *A61B 1/0057* (2013.01); *A61B 1/00135* (2013.01); *A61B 1/01* (2013.01); *A61B 1/012* (2013.01); *A61B 1/31* (2013.01)

(58) Field of Classification Search
CPC ..... A61B 1/005; A61B 1/0051; A61B 1/0052; A61B 1/0053; A61B 1/0056; A61B 1/0055; A61B 1/0057; A61B 1/0058; A61B 1/008
See application file for complete search history.

(56) References Cited

U.S. PATENT DOCUMENTS

| 4,353,358 A | 10/1982 | Emerson |
| 4,802,461 A | 2/1989 | Cho |
| 6,780,151 B2 | 8/2004 | Grabover et al. |
| 6,899,673 B2 | 5/2005 | Ogura et al. |

(Continued)

FOREIGN PATENT DOCUMENTS

| DE | 20 2009 012 795 U1 | 2/2010 |
| EP | 1 774 913 A1 | 4/2007 |

(Continued)

OTHER PUBLICATIONS

Notification of Transmittal of the International Search Report and the Written Opinion of the International Searching Authority, or the Declaration, dated Feb. 21, 2013, for corresponding application No. PCT/US2012/065166, 5p.

*Primary Examiner* — Timothy J Neal
(74) *Attorney, Agent, or Firm* — Brinks Gilson & Lione

(57) ABSTRACT

The exemplary embodiments illustrated provide the discovery of systems, methods, and apparatuses of endoscope stabilization devices for use with, for example, slim scopes, so as to provide, for example, a flexible outer structure capable of bending and holding a fixed position so as to provide, for example, support to make cannulation with a slim scope and target anatomy easier and more efficient.

18 Claims, 7 Drawing Sheets

(56) References Cited

U.S. PATENT DOCUMENTS

| | | |
|---|---|---|
| 7,008,375 B2 | 3/2006 | Weisel |
| 7,326,176 B2 | 2/2008 | Machiya et al. |
| 7,682,319 B2 | 3/2010 | Martin et al. |
| 8,821,477 B2 | 9/2014 | Northrup et al. |
| 2004/0162568 A1 | 8/2004 | Saadat et al. |
| 2005/0075653 A1 | 4/2005 | Saadat et al. |
| 2006/0041188 A1 | 2/2006 | Dirusso et al. |
| 2007/0083081 A1 | 4/2007 | Schlagenhauf et al. |
| 2007/0225562 A1* | 9/2007 | Spivey ................ A61B 17/068 600/121 |
| 2007/0244358 A1 | 10/2007 | Lee |
| 2008/0249364 A1 | 10/2008 | Korner |
| 2009/0177040 A1 | 7/2009 | Lyons et al. |
| 2010/0087711 A1 | 4/2010 | Edwards |
| 2010/0256446 A1 | 10/2010 | Raju |
| 2011/0046442 A1 | 2/2011 | Matsushita |
| 2011/0207999 A1 | 8/2011 | Torisawa et al. |
| 2012/0130173 A1 | 5/2012 | Lutze et al. |

FOREIGN PATENT DOCUMENTS

| | | |
|---|---|---|
| EP | 2 286 717 A1 | 2/2011 |
| WO | WO 2010/136275 A1 | 12/2010 |

\* cited by examiner

ENDOSCOPE STABILIZATION SYSTEM

RELATED APPLICATION

This application claims priority to U.S. Non-Provisional application Ser. No. 13/676,877, filed Nov. 14, 2012, now U.S. Pat. No. 9,585,546, which claims the benefit of priority from U.S. Provisional Application No. 61/562,137, filed Nov. 21, 2011, both of which are titled "Endoscope Stabilization System", the contents of which are incorporated herein by reference.

TECHNICAL FIELD

The present invention relates to medical devices and more specifically, endoscopes.

BACKGROUND

Endoscopes are routinely used to provide direct visualization to medical personnel while performing medical procedures. To enable medical personnel to reach smaller portions of the anatomy, medical personnel often use a mother-baby scope technique. Baby scopes are either fiber optic ocular lens scopes or electronic, and they typically have an outer diameter of 3.5 mm. Using a mother-baby scope technique, a baby scope is directed through a working channel of an endoscope, such as a forward-viewing gastroscope or a side-view duodenoscope, and thereafter directed to the targeted anatomy.

For example, endoscopic retrograde cholangiopancreatography (ERCP) is a commonly used endoscopic procedure to both diagnose and treat ailments of both the pancreatic and bile duct systems. Often, a side-viewing endoscope (duodenoscope) is advanced to the duodenum and in line with the ampulla of Vater (papilla) to facilitate diagnostic and therapeutic catheter-based procedures. A method to gain direct visualization of the bile and pancreatic ducts is use of a mother scope/baby scope system where the mother scope is a duodenoscope and the baby scope is a choledochoscope that is passed through the accessory channel of the duodenoscope.

The mother-baby scope approach presents numerous problems and issues. For example, the technique is difficult to use for a number of reasons, including but not limited to, requiring two sets of operators, two sets of equipment, and accordingly, additional resources. Moreover, due to the outer diameter size of the mother scope and the baby scope, the possible anatomical areas able to be visualized and treated by such an approach are limited.

Alternatively, rather than use a mother-baby scope approach, a slim scope may be considered. A slim scope has an outer diameter of approximately 5-7 mm, and therefore, it cannot be passed through the accessory channel of a duodenoscope. Instead, an overtube is used to provide structure for the slim scope to facilitate cannulation into the papilla.

The slim-scope approach presents numerous problems and issues. The technique is difficult to use for a number of reasons. For example, the overtubes that are used in conjunction with the slim scope cannot bend where the slim scope exits at the distal end of the overtube, nor can the distal end of the overtubes be held in a fixed position. As a result, the slim scope often falls out of the bile duct or other targeted anatomy because of its extra weight compared to a lighter baby scope.

BRIEF SUMMARY

In a first aspect, an overtube is provided, including a substantially tubular body having a proximal portion, a distal portion, and a lumen extending through the proximal portion and the distal portion; a plurality of ball bearings disposed within the lumen and coupled to the substantially tubular body, wherein the plurality of ball bearings are configured to freely spin; and a first plurality of notches disposed within the proximal portion of the substantially tubular body.

In a second aspect, an endoscope stabilization system is provided, including an endoscope having a viewing end; and an overtube having: a substantially tubular body having a proximal portion, a distal portion, and a lumen extending through the proximal portion and the distal portion, wherein the lumen of the overtube is configured for co-axial disposal about the viewing end of the endoscope; a plurality of ball bearings disposed within the lumen and coupled to the substantially tubular body, wherein the plurality of ball bearings are configured to freely spin; and a first plurality of notches disposed within the proximal portion of the substantially tubular body.

In a third aspect, a method for using an endoscope stabilization system is provided, including providing an endoscope having a viewing end; and providing an overtube having: a substantially tubular body having a proximal portion, a distal portion, and a lumen extending through the proximal portion and the distal portion; a plurality of ball bearings disposed within the lumen and coupled to the substantially tubular body, wherein the plurality of ball bearings are configured to freely spin; a first plurality of notches disposed within the proximal portion of the substantially tubular body; and a steering means for deflecting a portion of the substantially tubular body; disposing the viewing end of the endoscope through the lumen of the substantially tubular body forming an assembly; directing the assembly to a target area; and performing a diagnostic or therapeutic procedure.

BRIEF DESCRIPTION OF THE SEVERAL VIEWS OF THE DRAWINGS

The embodiments will be further described in connection with the attached drawing figures. It is intended that the drawings included as a part of this specification be illustrative of the exemplary embodiments and should in no way be considered as a limitation on the scope of the invention. Indeed, the present disclosure specifically contemplates other embodiments not illustrated but intended to be included in the claims. Moreover, it is understood that the figures are not necessarily drawn to scale.

DETAILED DESCRIPTION OF PRESENTLY PREFERRED EMBODIMENTS

Figure 1:
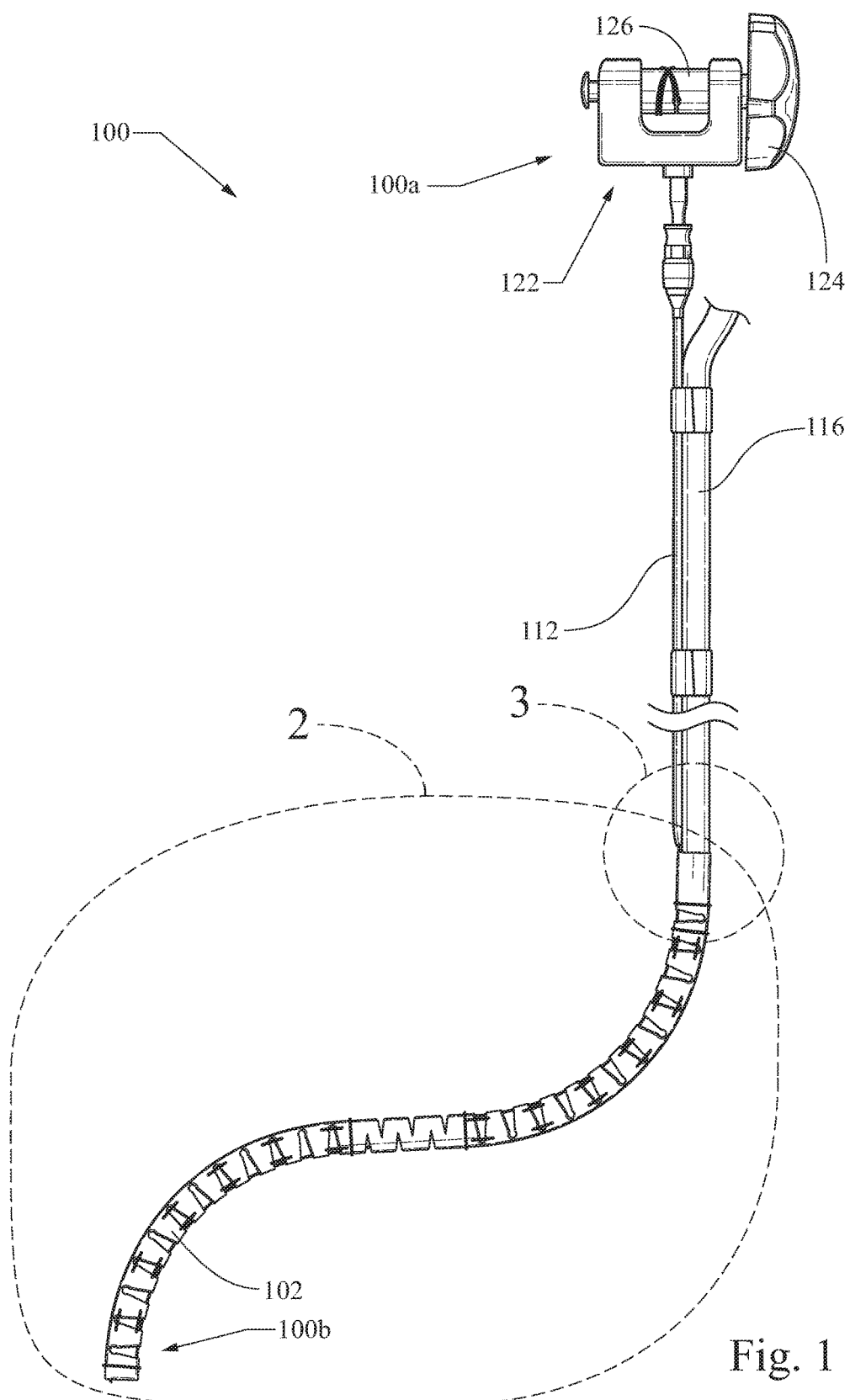
FIG. 1 illustrates a perspective view of an exemplary endoscope stabilization system.

The exemplary embodiments illustrated provide the discovery of systems, methods, and apparatuses of endoscope stabilization devices for use with, for example, slim scopes, so as to provide, for example, a flexible outer structure capable of bending and holding a fixed position so as to provide, for example, support to make cannulation with a slim scope and target anatomy easier and more efficient. Embodiments of systems, apparatuses, methods, and equivalents thereto provide many benefits, including but not limited to, better navigation to and stabilization at a targeted anatomy.

Diseases and conditions contemplated for treatment include, but are not limited to, those involving the gastrointestinal region, esophageal region, duodenum region, biliary region, colonic region, as well as any other bodily region or field benefiting from direct visualization of or access to a target site for performing a diagnostic and/or therapeutic procedure.

The present invention is not limited to those embodiments illustrated herein, but rather, the disclosure includes all equivalents including those of different shapes, sizes, and configurations, including but not limited to, other types of visualization catheters, endoscopes, and component parts. The systems, devices, and methods may be used in any field benefiting from a visualization catheter, endoscopes, or parts used in conjunction with visualization catheters and endoscopes. Additionally, the devices and methods are not limited to being used with human beings; others are contemplated, including but not limited to, animals.

Unless otherwise defined, all technical and scientific terms used herein have the same meaning as commonly understood by one of ordinary skill in the art. In case of conflict, the present document, including definitions, will control. Preferred methods and materials are illustrated below, although apparatuses, methods, and materials similar or equivalent to those illustrated herein may be used in practice or testing. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

The term "proximal," as used herein, refers to a direction that is generally towards a physician during a medical procedure.

The term "distal," as used herein, refers to a direction that is generally towards a target site within a patient's anatomy during a medical procedure.

A more detailed description of the embodiments will now be given with reference to FIGS. 1-8. Throughout the disclosure, like reference numerals and letters refer to like elements. The present disclosure is not limited to the embodiments illustrated; to the contrary, the present disclosure specifically contemplates other embodiments not illustrated but intended to be included in the claims.

Figure 2:
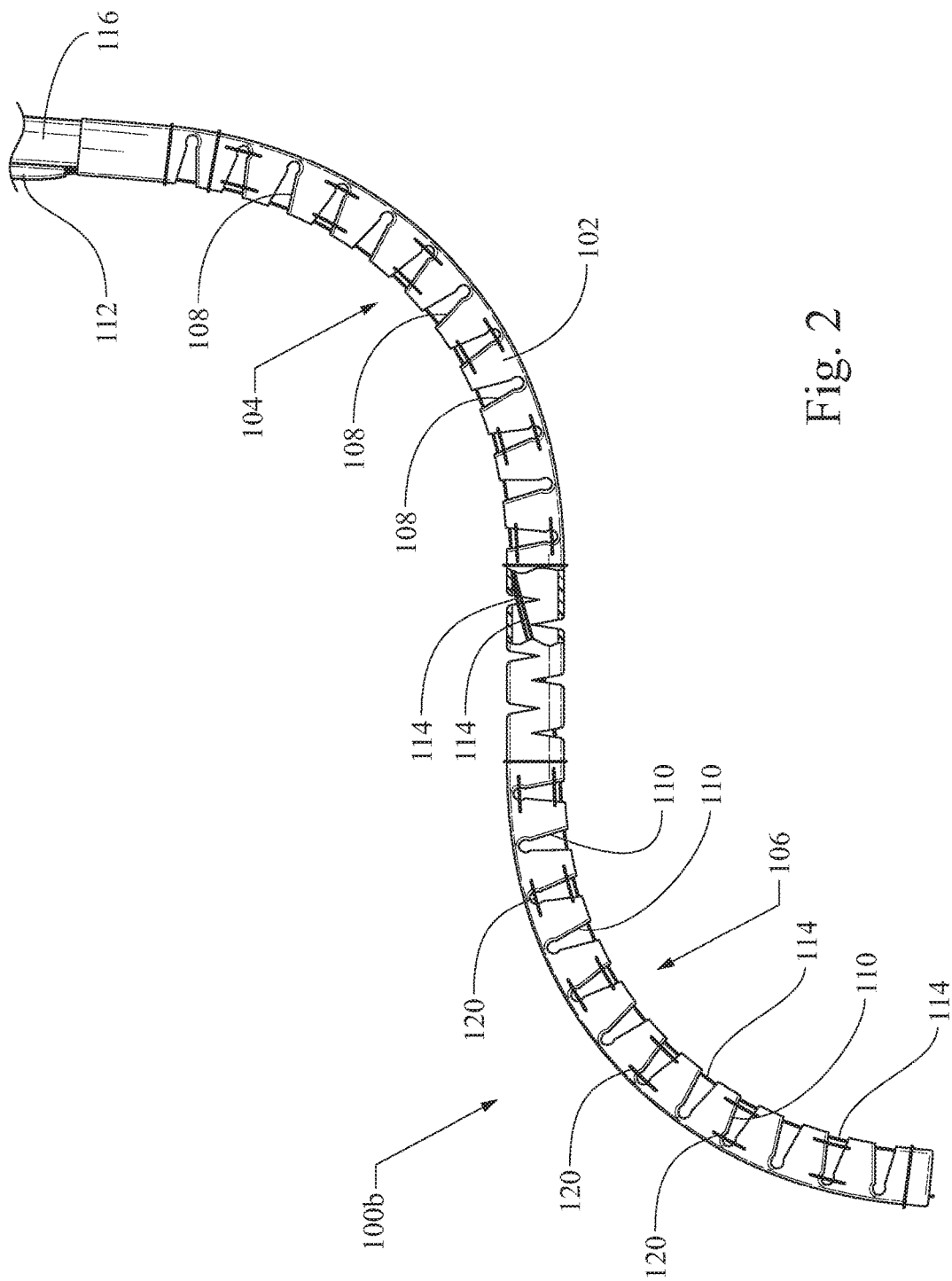
FIG. 2 illustrates a perspective view of the distal portion of the exemplary endoscope stabilization system illustrated in FIG. 1 at the dashed-circle 2.
Figure 3:
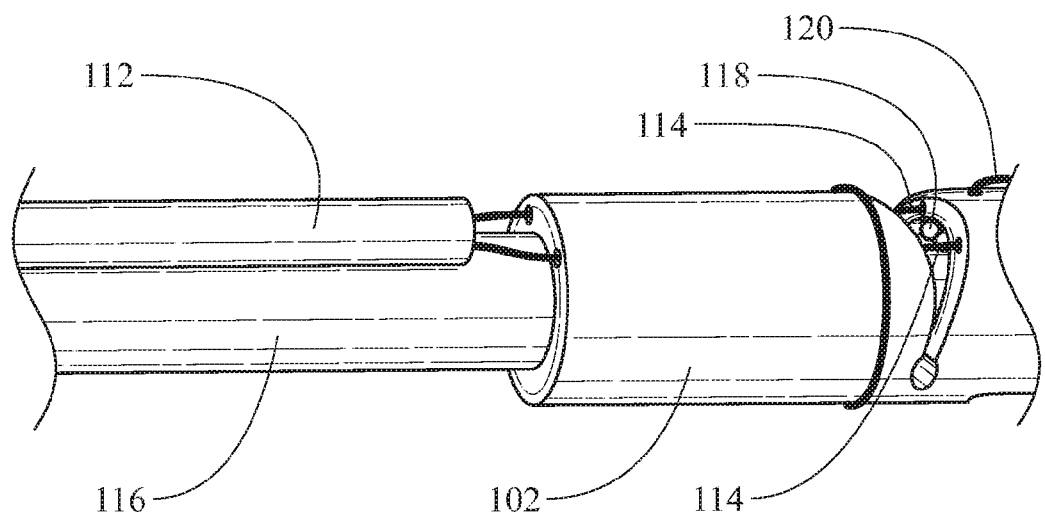
FIG. 3 illustrates a perspective view of a portion of the exemplary endoscope stabilization system illustrated in FIG. 1 at the dashed-circle 3.
Figure 4:
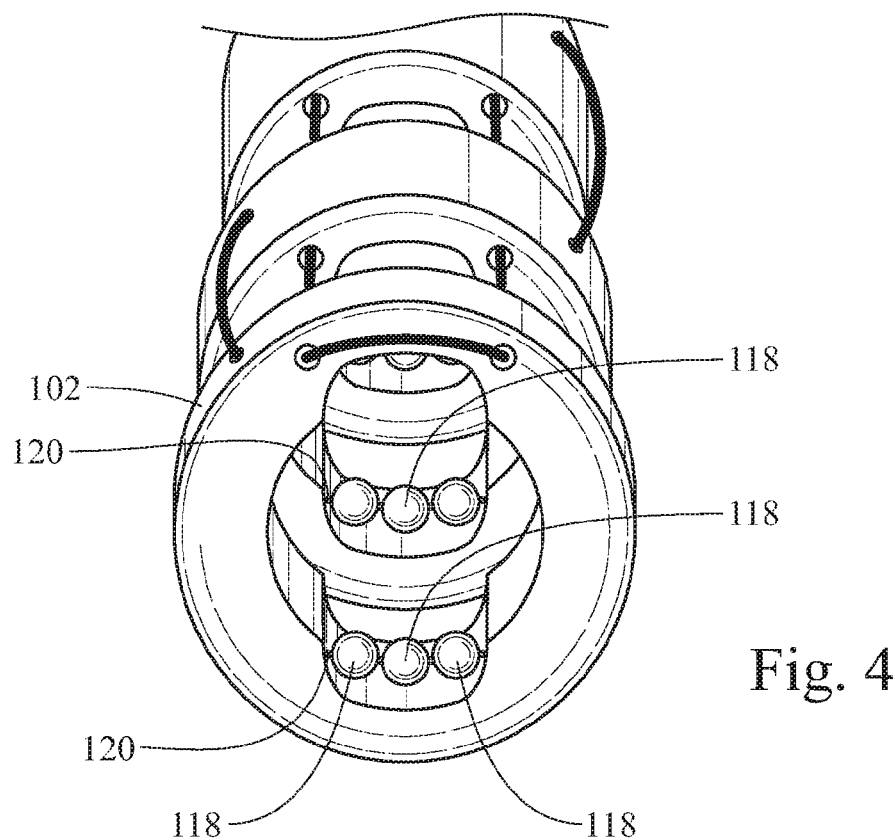
FIG. 4 illustrates a perspective view inside an exemplary overtube of the exemplary endoscope stabilization system illustrated in FIG. 1.
Figure 5:
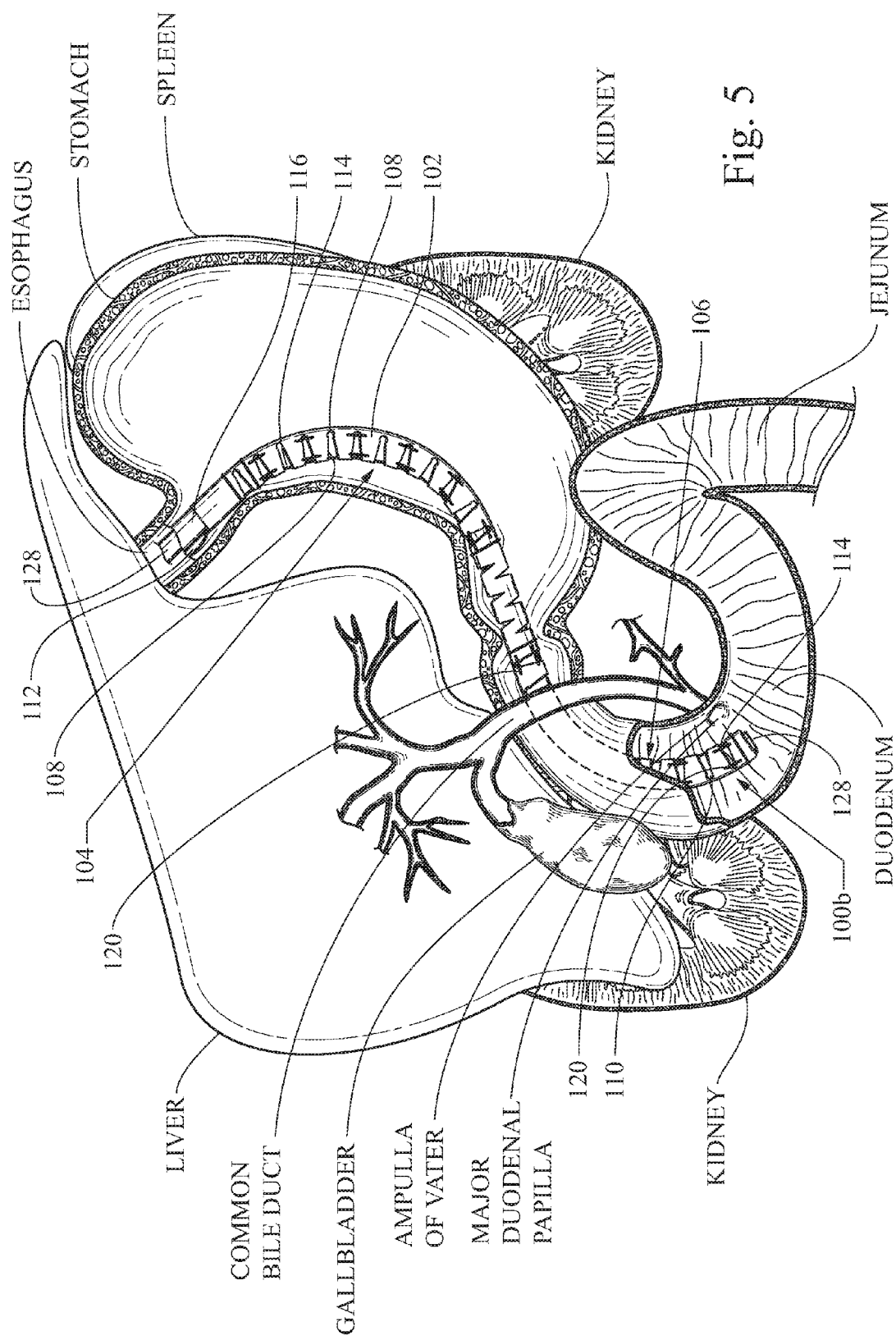
FIG. 5 illustrates the distal portion of the exemplary stabilization system illustrated in FIG. 1 in use.

FIG. 1 illustrates a perspective view of exemplary endoscope stabilization system 100, FIG. 2 illustrates a perspective view of distal portion 100*b* of exemplary endoscope stabilization system 100 illustrated in FIG. 1 at the dashed-circle 2, FIG. 3 illustrates a perspective view of a portion of exemplary endoscope stabilization system 100 illustrated in FIG. 1 at the dashed-circle 3, FIG. 4 illustrates a perspective view inside exemplary overtube 102 of exemplary endoscope stabilization system 100, and FIG. 5 illustrates distal portion 102 of exemplary stabilization system 100 in use. Referring to FIGS. 1-5, endoscope stabilization system 100 includes proximal portion 100*a* and distal portion 100*b*. Although illustrated for use with a slim scope, endoscope stabilization system 100 and equivalents thereof are contemplated for use with other endoscopes, visualization catheters, and medical instruments so as to improve the navigation and stabilization of a diagnostic or therapeutic instrument to any target site.

Exemplary endoscope stabilization system 100 and equivalents thereof provide numerous advantages and overcomes the disadvantages of using a slim scope, such as the problem of a slim scope not being able to bend where it exits at the distal end of a traditional overtube, a slim scope not being able to be held in a fixed position, and a slim scope falling out from the target anatomy, such as the bile duct because of its extra weight compared to a lighter baby scope.

The distal viewing portion of a slim scope is inserted into slim scope conduit 116 and through the lumen of overtube 102. Overtube 102 is a flexible, substantially tubular body having a lumen disposed there though. Overtube 102 includes a number of notches to aid in flexibility and bendability at strategic locations along overtube 102 so as to coincide with the anatomy through which overtube 102 will traverse. Overtube 102 has an outer diameter of about 0.56 inches although other configurations are contemplated.

Overtube 102 is connected to slim scope conduit 116. Overtube 102 includes top side notches 108 along first bend 104 and bottom side notches 110 along second bend 106, as illustrated in FIG. 2. Top side notches 108 and bottom side notches 110 preferably are about triangular in shape and have an angle of about 30 degrees. Other configurations and dimensions are contemplated, including but not limited to, an angle of about 1-90 degrees for one or more notches.

Top side notches 108 aid in permitting overtube 102 to bend at first bend 104. Bottom side notches 110 aid in permitting overtube 102 to bend at second bend 106. First bend 104 and second bend 106 are more flexible than the remainder of overtube 102. Portions of overtube 102 not contemplated to achieve significant bending have fewer or no notches so as to provide additional stability and less flexibility. Other bending configurations are contemplated, including configuring overtube 106 with zero or more bends so as to align with the pathway of the target anatomy. Other overtube configurations are also contemplated. For example, one or more overtubes may be configured so that the device may bend around the lesser curvature of the stomach as well as the duodenal bend after the pylorus to better navigate to the papilla (or other target anatomy).

As best illustrated in FIGS. 1-3, overtube 102 is equipped with steering means, such as two-way steering wires 114. Steering wires 114 are disposed within the luminal wall of overtube 102 to create a loop at the distal end of overtube 102, such that they provide a means for two-way deflection of overtube 102. For example, when steering wires 114 are retracted at the user end, overtube 102 flexes and deflects to the desired degree according to the patient's anatomy and the user's preference. Proximal portions of steering wires 102 enter steering wire tubing 112 coupled near slim scope conduit 116 and travel through steering wire tubing 112 and exit at a proximal portion of steering wire tubing 112. The proximal portion of overtube 102 is press-fit with the distal portion of steering wire tubing 112 as best illustrated in FIG. 3. Other means for coupling are contemplated. Steering wire tubing 112 is preferably a 24 French Cook Flexor (available from Cook Medical, Bloomington Ind.), although other tubing is contemplated, including but not limited to extruded tubing and tubing made from numerous materials, including but not limited to, polyethylene, polytetrafluoroethylene (PTFE), expanded PTFE (EPTFE), a catheter that is overmolded over a coil spring, and nylon.

Steering wires 114 are optionally connected to handle 122, as best illustrated in FIG. 1, and may be wound or unwound along axel 126 by turning knob 124 in either direction so as to wind or unwind steering wires 114, thereby pushing or pulling steering wires 114 and causing all or a portion of overtube 102 to deflect. Other handle configurations are contemplated. Because a slim scope is disposed through slim scope conduit 116 and overtube 102, as overtube 102 is deflected, so, too, is the slim scope.

Alternative steering means are contemplated, including the use of one or more steering wires; one or more steering wires disposed adjacent to the luminal wall of overtube 102; one or more steering wires housed within an attachment that extends externally along overtube 102; and one or more steering wires surrounded by a coating on the exterior wall surface of overtube 102. Coatings contemplated include, but are not limited to, polytetrafluoroethylene (PTFE) or other materials having low coefficients of friction. Additional steering means are contemplated, including but not limited to, configuring an overtube (such as those illustrated herein and equivalents thereto) with other steering/drive wires and/or pneumatic controls used alone or in combination with other steering means. If the overtube is configured with two overtubes, multiple deflection wires may be utilized so as to cause the overtubes to flex simultaneously or independently so that the overtubes can flex at the same or different degrees relative to each other.

Overtubes illustrated and equivalents thereto may be manufactured by numerous means, including but not limited to, stereolithography apparatus (SLA) using, for example, DSM Somos® 8120 Resin (available from DSM, Elgin, Ill.) or other materials, including but not limited to, liquid photopolymers that produce flexible components.

Overtubes illustrated and equivalents thereto may further comprise one or more rigid portions and one or more portions more flexible than the one or more rigid portions. The one or more flexible portions may be configured to aid in steering. For example, the one or more flexible portions may comprise one or more vertebrae modules. Alternatively, the one or more flexible portions may comprise ribs. Alternatively, the one or more flexible portions may comprise grooves or cuts disposed into the same material as that of the one or more rigid portions. Alternatively, overtubes illustrated and equivalents thereto may be configured with a first rigid portion, a second portion configured for flexibility and steering ease, and a third portion configured similar to a standard flexible catheter. Alternatively, overtubes illustrated and equivalents thereto may be configured with a soft portion and a rigid portion, wherein the interiors of each section change throughout the device to aid with steering or to achieve other benefits.

As best illustrated in FIG. 4, disposed within overtube 102 are one or more optional ball bearings 118 that reduce the friction of overtube 102 against the slim scope and improve the lateral back and forth movement of the slim scope within overtube 102. Ball bearings 118 are coupled to overtube 102 so as to spin freely. For example, ball bearings 118 may be coupled to overtube 102 by an attachment means, including but not limited to, coring each of ball bearings 118 and threading each therethrough with suture wire 120 and connecting suture wire 120 to overtube 102. Other attachment means are contemplated, including but not limited to, other wires, fibers, threads, one or more flexible stylets, or combination thereof.

Ball bearings 118 are made from metal but may be made from numerous other materials, including but not limited to, plastics or any combination thereof. As illustrated in FIG. 4, ball bearings 118 are about 1-2 mm in diameter; other sizes are contemplated so as to minimize friction and facilitate movement of a slim scope through each of bends 104, 106 of overtube 102.

It is contemplated that distal portion 100 of endoscope stabilization system be coupled to a slim scope such that the distal portion of a slim scope is inserted into overtube 102. Although illustrated for use with a slim scope 116, endoscope stabilization system 100 and equivalents thereof are contemplated for use with other endoscopes, visualization catheters, and medical instruments so as to improve the navigation and stabilization of a diagnostic or therapeutic instrument to any target site.

The assembly of a slim scope disposed within slim scope conduit 116 and overtube 102 is directed to a target site. For example, the assembly may be directed through a patient's mouth and to, for example, the ampulla of Vater and/or the major duodenal papilla. For example, to use endoscope stabilization system 100, a wire guide is directed to a target site. A slim scope is then loaded onto the wire guide, and overtube 102 is placed over the slim scope. The assembly is then loaded onto the wire guide and navigated to the target site.

As best illustrated in FIG. 5, when manufactured for use in navigating slim scope 128 through the esophagus, stomach, and common bile duct of a human being so as to access, for example, the ampulla of Vater and/or the major duodenal papilla, first bend 104 of overtube 102 preferably is configured to align with the bend from the esophagus to the stomach, and second bend 106 of overtube 102 is preferably configured to align with the bend from the stomach to the common bile duct. Overtube 102 provides support to slim scope 128 and is capable of bending, as with first bend 104 and second bend 106 as well as two or more way deflection using steering wires 114, so as to navigate and hold slim scope 128 in a fixed position while supporting the same. Accordingly, cannulation with slim scope 128 to the target anatomy is easier and more efficient, and slim scope 128 is less likely to inadvertently move or fall out from the target anatomy.

Figure 6:
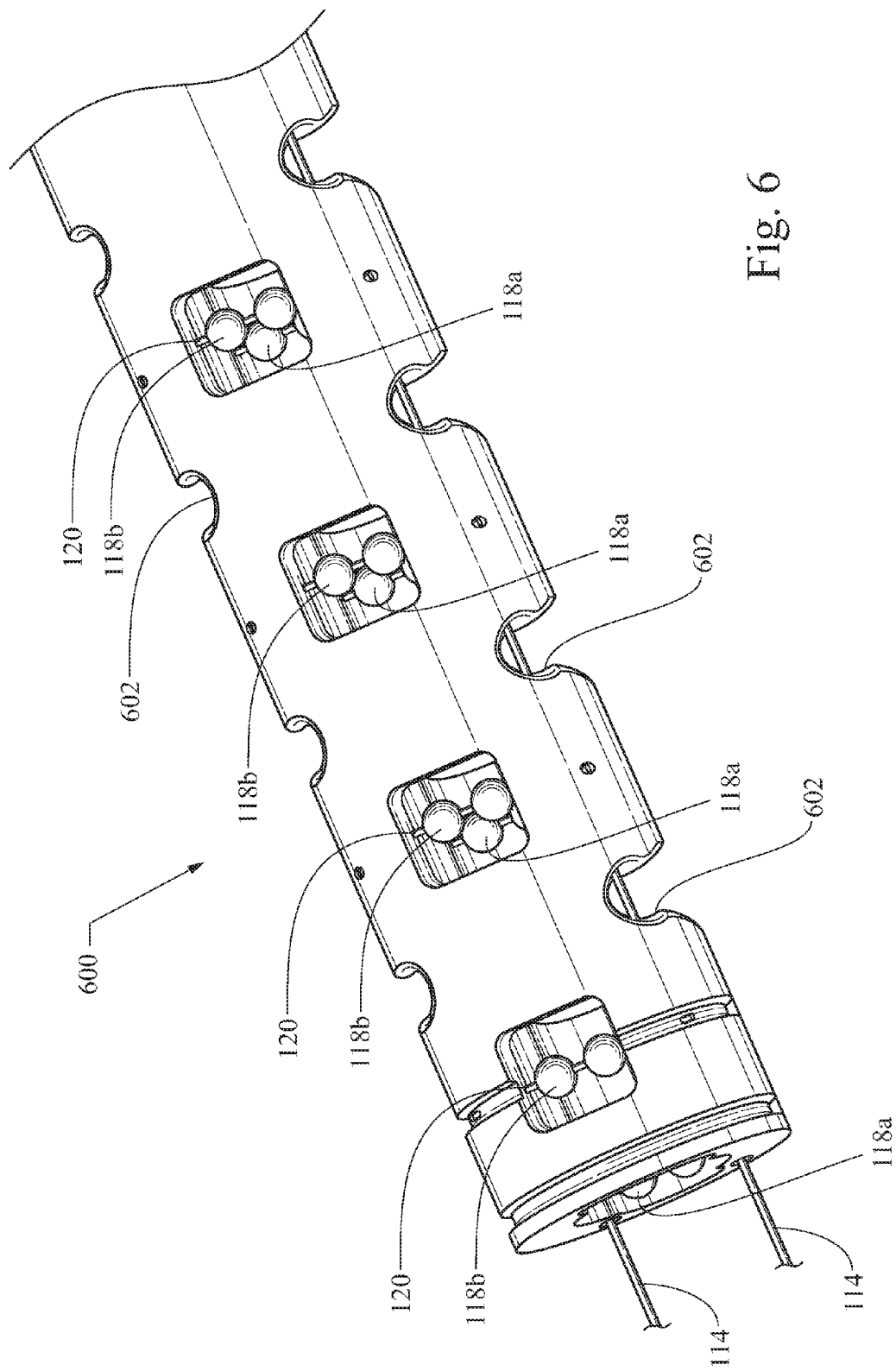
FIG. 6 illustrates a perspective view of another embodiment of an exemplary overtube of an exemplary endoscope stabilization system.

FIG. 6 illustrates a perspective view of another embodiment of exemplary overtube 600 of an exemplary endoscope stabilization system. Overtube 600 includes notches 602 similar to that of overtube 102 (illustrated in FIG. 2). Notches 602 preferably are about triangular in shape and have an angle of about 30 degrees. Other configurations and dimensions are contemplated, including but not limited to, an angle of about 1-90 degrees for one or more notches.

Top ball bearings 118b and bottom ball bearings 118a of overtube 600 are strategically located within overtube 600 so as to better reduce slim scope friction at bends. For example, top ball bearings 118b and bottom ball bearings 118a of overtube 600 are located on both the top and bottom interior portion of overtube 600 such that they sandwich a slim scope therethrough.

Figure 7:
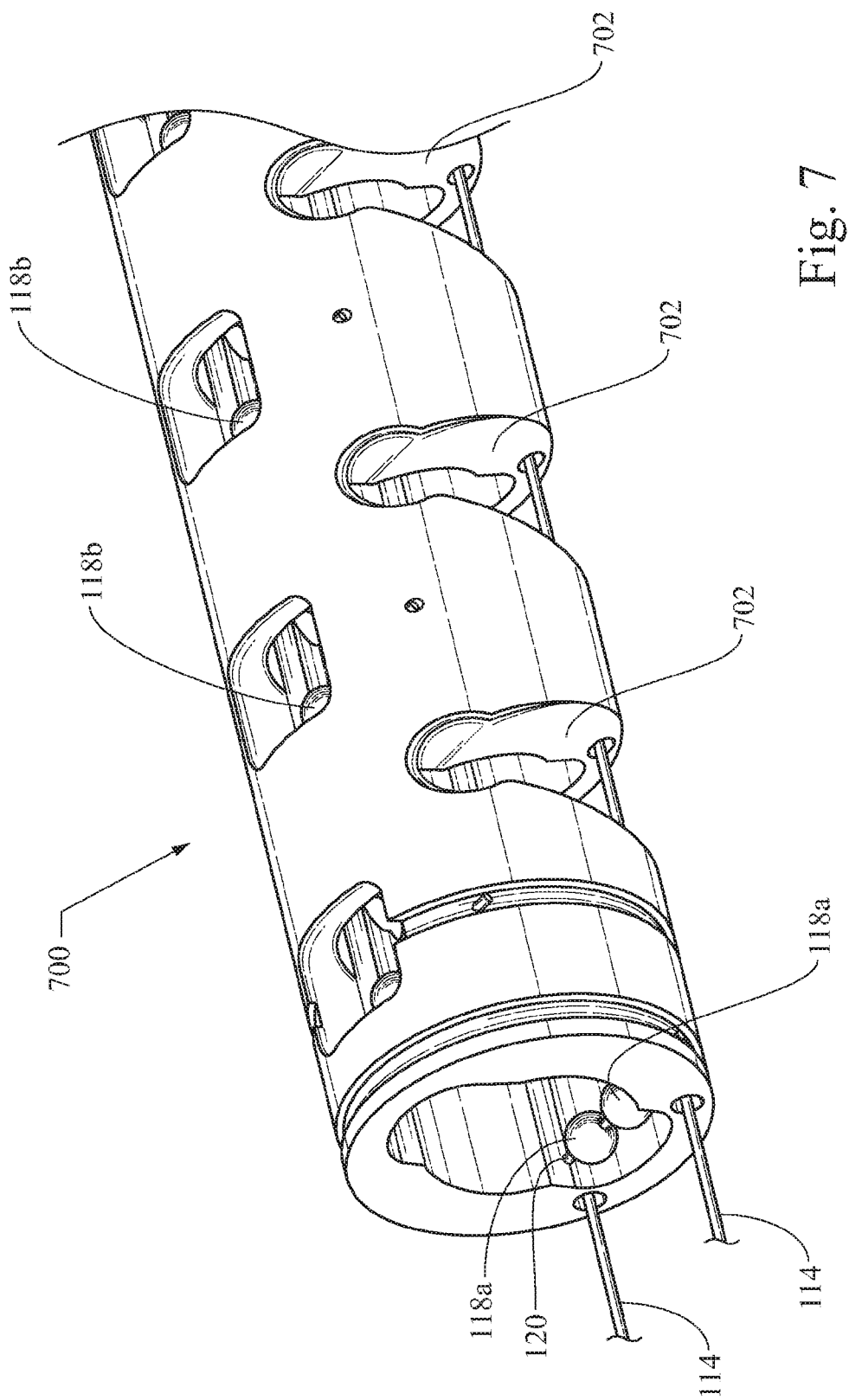
FIG. 7 illustrates a perspective view of another embodiment of an exemplary overtube of an exemplary endoscope stabilization system.

FIG. 7 illustrates a perspective view of another embodiment of exemplary overtube 700 of an exemplary endoscope stabilization system. Overtube 700 includes notches 702 similar to that of overtube 102. Other notch 702 configurations are contemplated. Disposed within overtube 702 are strategically located top ball bearings 118b and bottom ball bearings 118a so as to better reduce slim scope friction at bends. For example, bottom ball bearings 118a of overtube 700 are configured to communicate with the bottom surface of a slim scope and top ball bearings 118b are configured to communicate with the top surface of a slim scope.

Figure 8:
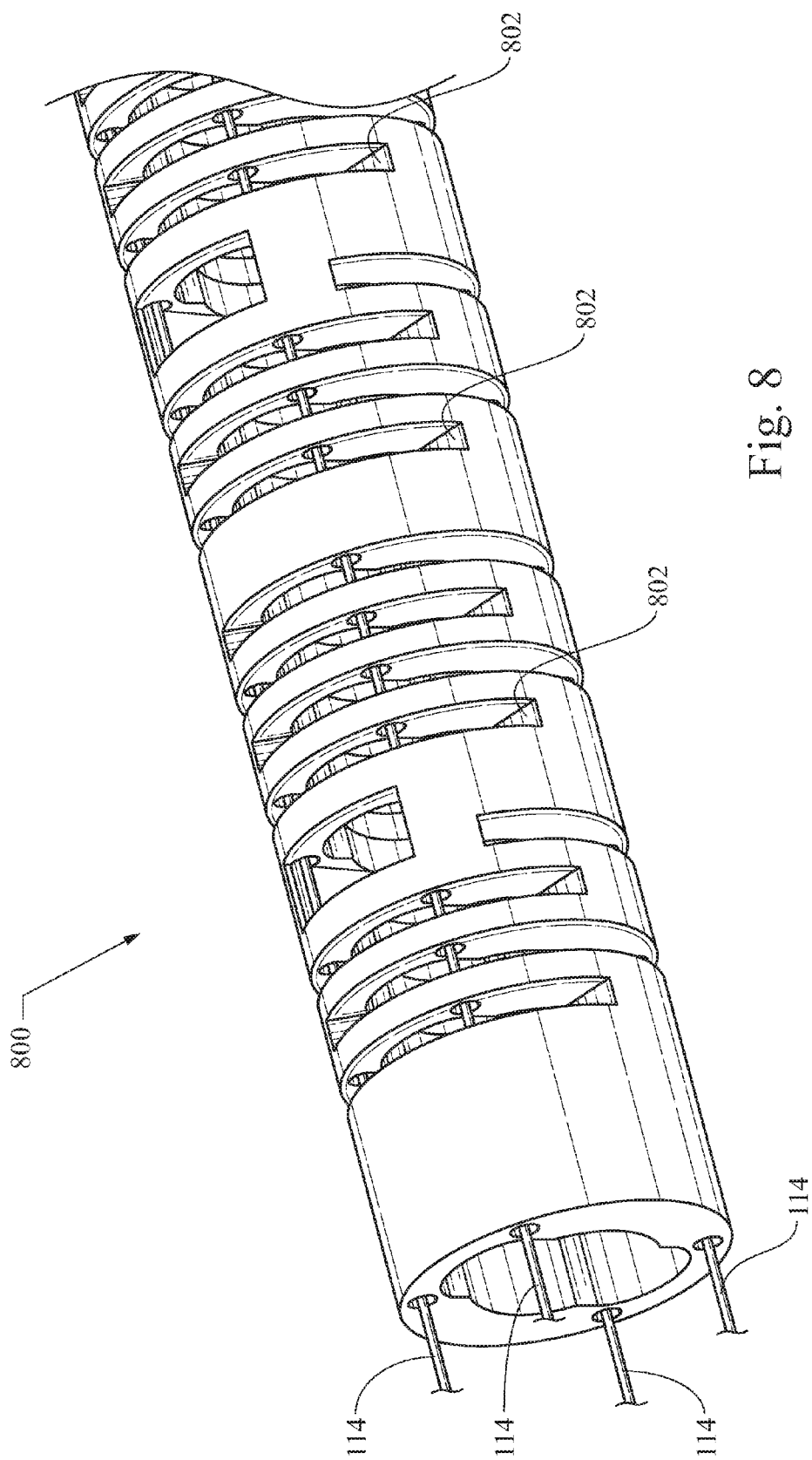
FIG. 8 illustrates a perspective view of another embodiment of an exemplary overtube of an exemplary endoscope stabilization system.

FIG. 8 illustrates a perspective view of another embodiment of exemplary overtube 800 of an exemplary endoscope stabilization system. Overtube 800 includes four deflection wires 114 within the wall of overtube 800 so as to provide for four-way steering and deflection. As with other embodiments illustrated, each of wires 114 travels through overtube 800 and connects to a handle to provide for four-way steering and deflection. Notches 802 disposed into the surface of overtube 800 are circumferential and provides for flexibility of overtube 800 in all directions. Other notch 802 configurations are contemplated. Overtube 800 may also include one or more ball bearings as illustrated with other embodiments.

From the foregoing, the discovery of systems, apparatuses, and methods to provide endoscope stabilization provides numerous benefits to the medical field, including but not limited to, easier and more efficient navigation to and stabilization at a target site. It can be seen that the embodiments illustrated and equivalents thereto as well as the methods of manufacturer may utilize machines or other resources, such as human beings, thereby reducing the time, labor, and resources required to manufacturer the embodiments. Indeed, the discovery is not limited to the embodiments illustrated herein, and the principles and methods illustrated herein may be applied and configured to any visualization catheter, endoscope, and equivalents.

Those of skill in the art will appreciate that embodiments not expressly illustrated herein may be practiced within the scope of the present discovery, including that features illustrated herein for different embodiments may be combined with each other and/or with currently-known or future-developed technologies while remaining within the scope of the claims presented here. It is therefore intended that the foregoing detailed description be regarded as illustrative rather than limiting. It is understood that the following claims, including all equivalents, are intended to define the spirit and scope of this discovery. Furthermore, the advantages illustrated above are not necessarily the only advantages of the discovery, and it is not necessarily expected that all of the illustrated advantages will be achieved with every embodiment of the discovery.

What is claimed is:

1. An overtube for use with an endoscope, the overtube comprising:

a substantially tubular body comprising a proximal portion, a distal portion, and a lumen extending through the proximal portion and the distal portion, the lumen being configured for the passage of an endoscope there through;

a first plurality of notches disposed within a surface of the substantially tubular body, the first plurality of notches being disposed along a first side of the substantially tubular body and configured to bend the substantially tubular body along a first curvilinear pathway;

a second plurality of notches disposed within the surface of the substantially tubular body and spaced longitudinally apart from the first plurality of notches, the second plurality of notches being disposed along a second side of the substantially tubular body, the second plurality of notches being configured to bend the substantially tubular body along a second curvilinear pathway that is different from the first curvilinear pathway, and a steering wire comprising a proximal steering wire portion and a distal steering wire portion, the distal steering wire portion being coupled to the substantially tubular body along both the first plurality of notches and the second plurality of notches, wherein the steering wire is configured to simultaneously deflect the substantially tubular body along both the first curvilinear pathway and the second curvilinear pathway when the proximal steering wire portion is pulled in a proximal direction, and wherein the distal steering wire portion comprises a first distal wire portion disposed along the first side of the substantially tubular body, and a second distal wire portion disposed along the second side of the substantially tubular body, wherein the first and second distal wire portions are configured to simultaneously deflect the substantially tubular body along both the first and second curvilinear pathways when the proximal steering wire portion is pulled in the proximal direction.

2. The overtube of claim 1, wherein the substantially tubular body comprises a plurality of roller elements at least partially disposed within the lumen, the plurality of roller elements being configured to engage and facilitate the passage of the endoscope through the lumen.

3. The overtube of claim 2, wherein the plurality of roller elements comprises a plurality of rotatable ball bearings distributed along a substantial length of the lumen at spaced apart locations.

4. The overtube of claim 2, wherein the plurality of roller elements comprises a plurality of adjacent pairs of ball bearings that are configured to sandwich at least a portion of an endoscope disposed through the lumen of the substantially tubular body.

5. The overtube of claim 1, wherein the first plurality of notches and the second plurality of notches each comprise an asymmetric configuration relative to a cross-section of the substantially tubular body, wherein the asymmetric configuration of the first plurality of notches is oriented along a first radial direction, and wherein the asymmetric configuration of the second plurality of notches is oriented along a second radial direction that is different from the first radial direction.

6. The overtube of claim 5, wherein the second radial direction is opposite the first radial direction.

7. The overtube of claim 1, wherein the distal steering wire portion further comprises an intermediate distal wire portion connected between the first distal wire portion and the second distal wire portion, intermediate distal wire portion extending between the first and second sides of the substantially tubular body.

8. The overtube of claim 1, wherein the steering wire is configured to simultaneously deflect the substantially tubular body along an S-shaped pathway.

9. The overtube of claim 1, further comprising a handle comprising a knob connected to an axel, wherein the proximal steering wire portion is attached to the axel, and wherein the knob is configured to rotate the axel to wind or unwind the proximal steering wire portion.

10. An endoscope stabilization system comprising:
an endoscope comprising a viewing end; and
an overtube comprising:
a substantially tubular body comprising a proximal portion, a distal portion, and a lumen extending through the proximal portion and the distal portion, wherein the endoscope is movably disposed through the lumen of the overtube;
a first plurality of notches disposed within a surface of the substantially tubular body, the first plurality of notches being disposed along a first side of the substantially tubular body and configured to bend the substantially tubular body along a first curvilinear pathway; and
a second plurality of notches disposed within the surface of the substantially tubular body and spaced longitudinally apart from the first plurality of notches, the second plurality of notches being disposed along a second side of the substantially tubular body, the second plurality of notches being configured to bend the substantially tubular body along a second curvilinear pathway that is different from the first curvilinear pathway,
wherein the overtube further comprises steering means coupled to the substantially tubular body and configured to simultaneously deflect a portion of the substantially tubular body along both the first curvilinear pathway and the second curvilinear pathway, and
wherein the steering means comprises a steering wire having a proximal steering wire portion and a distal steering wire portion, the distal steering wire portion comprising a first distal wire portion that is coupled to and disposed along the first side of the substantially tubular body, and a second distal wire portion that is coupled to and disposed along the second side of the substantially tubular body, the first distal wire portion being disposed within a first luminal wall of the substantially tubular body and the second distal wire portion being disposed within a second luminal wall of the substantially tubular body that is opposite the first luminal wall, wherein the first and second distal wire portions are configured to simultaneously deflect the substantially tubular body along both the first and second curvilinear pathways when the proximal steering wire portion is pulled in the proximal direction.

11. The endoscope stabilization system of claim 10, wherein the substantially tubular body comprises a plurality of roller elements coupled to an interior surface of the substantially tubular body and at least partially extending into the lumen, the plurality of roller elements being configured to engage and facilitate axial movement of the endoscope through the lumen.

12. The endoscope stabilization system of claim 11, wherein the plurality of roller elements comprises a plurality of ball bearings distributed at spaced apart locations along both the proximal portion and the distal portion of the lumen, the plurality of ball bearings being configured to engage the endoscope and freely spin to facilitate movement of the endoscope through the lumen.

13. The endoscope stabilization system of claim 10, wherein the first plurality of notches and the second plurality of notches each comprise an asymmetric configuration relative to a cross-section of the substantially tubular body, the asymmetric configuration of the first plurality of notches being oriented along a first radial direction, and the asymmetric configuration of the second plurality of notches being oriented along a second radial direction that is different than the first radial direction.

14. The endoscope stabilization system of claim 10, wherein the distal steering wire portion further comprises an intermediate distal wire portion connected between the first distal wire portion and the second distal wire portion, intermediate distal wire portion extending between the first and second sides of the substantially tubular body.

15. The endoscope stabilization system of claim 14, wherein the proximal portion of the substantially tubular body is coupled to a handle, the handle comprising a rotatable knob and axel, wherein the proximal steering wire portion is operably connected to the axel, and wherein the rotation of the knob causes movement of the proximal steering wire portion relative to the substantially tubular body.

16. The endoscope stabilization system of claim 10, wherein the steering means is configured to simultaneously deflect the substantially tubular body along an S-shaped pathway.

17. The endoscope stabilization system of claim 10, wherein the viewing end of the endoscope is disposed through the lumen of the substantially tubular body.

18. The endoscope stabilization system of claim 10, wherein the endoscope comprises a slim scope having a diameter of about 5-7 mm.

* * * * *